United States Patent [19]

Buzzetti et al.

[11] Patent Number: 5,502,044
[45] Date of Patent: Mar. 26, 1996

[54] FLUORINATED 4-AMINOANDROSTADIENONE DERIVATIVES AND PROCESS FOR THEIR PREPARATION

[75] Inventors: Franco Buzzetti, Monza; Antonio Longo; Enrico Di Salle, both of Milan, all of Italy

[73] Assignee: Farmitalia Carlo Erba S.r.l., Milan, Italy

[21] Appl. No.: 195,205

[22] Filed: Feb. 14, 1994

[30] Foreign Application Priority Data

Feb. 18, 1993 [GB] United Kingdom ............ 9303306
Oct. 29, 1993 [GB] United Kingdom ............ 9322378

[51] Int. Cl.[6] .................... C07J 41/00; A61K 31/56
[52] U.S. Cl. .................... 514/177; 552/515; 514/178
[58] Field of Search .................... 552/515; 514/177

[56] References Cited

U.S. PATENT DOCUMENTS 4,408,616 10/1983 Duffy et al. .
4,757,061 7/1988 Faustini et al. .
4,822,528 4/1989 Colombo et al. .
4,824,830 4/1989 Buzzetti et al. .
4,873,233 10/1989 Villa et al. .

FOREIGN PATENT DOCUMENTS 0260975 3/1988 European Pat. Off. .
0291290 11/1988 European Pat. Off. .
2171100 8/1986 United Kingdom .

Primary Examiner—Rebecca Cook
Attorney, Agent, or Firm—Oblon, Spivak, McClelland, Maier & Neustadt

[57] ABSTRACT

The present invention relates to a compound of formula (I)

wherein (x) and (y) are single or double bonds;
A is a $$\diagdown C=O \quad \text{or} \quad \diagdown C \sim OR;$$

R and $R^3$ are hydrogen or acyl;
$R^1$ is hydrogen or fluorine;
and wherein:
when (y) is a single bond, $R^2$ is hydrogen, fluorine methyl, trifluoromethyl;
when (y) is a double bond, $R^2$ is methylene provided that when one of (x) or (y) is a double bond the other is a single bond and at least one of $R_1$ and $R_2$ is fluorine or trifluoromethyl or a pharmaceutically acceptable salt thereof. The compounds of formula (I) are useful as aromatase inhibitors.

6 Claims, No Drawings

FLUORINATED 4-AMINOANDROSTADIENONE DERIVATIVES AND PROCESS FOR THEIR PREPARATION

The present invention relates to new fluorinated 4-aminoandrostadienone derivatives, to a process for their preparation, to pharmaceutical compositions containing them, and to their use as therapeutic agents, in particular in the treatment of hormone-dependent diseases in mammals.

Basic and clinical data indicate that aromatized metabolites of androgens, i.e. the estrogens, are the hormones involved in the pathogenic cellular changes associated with the growth of some hormone-dependent cancers, such as breast, endometrial and ovarian carcinomas.

Estrogens are also involved in the pathogenesis of benign prostatic hyperplasia.

Endogenous estrogens are ultimately formed from either androstenedione or testosterone as immediate precursors.

The reaction of central importance is the aromatization of the steroidic ring A, which is performed by the enzyme aromatase. As aromatization is a unique reaction and the last in the series of steps in the biosynthesis of estrogens, it has been envisaged that an effective inhibition of the aromatase, resulting from compounds able to interact with the aromatizing steps, may have useful application for controlling the amount of circulating estrogens, estrogen-dependent processes in reproduction, and estrogen-dependent tumours. Known steroidal substances which have been reported to be endowed with an aromatase-inhibiting action are, for example, Δ'-testololactone (U.S. Pat. No. 2,744,120), 4-hydroxyandrost-4-ene-3,17-dione and esters thereof (see, for example, U.S. Pat. No. 4,235,893), 10-(1,2-propadienyl)-estr-4-ene-3,17-dione (U.S. Pat. No. 4,289,762), 10-(2-propynyl)estr-4-ene-3,17-dione (J. Amer. Chem. Soc., 103, 3221 (1981) and U.S. Pat. No. 4,322,416), 19-thioandrostene derivatives (Europ. Pat. Appl. 100,566), androsta-4,6-diene-3,17-dione, androsta-1,4,6-triene-3,17-dione (UK. Pat. Appl. 2,100,601A), androsta-1,4-diene-3,17-dione (Cancer Res. (Suppl.) 42, 3327 (1982)), 6-alkenylen-androsta-1,4-diene-3,17-diones (U.S. Pat. No. 4,808,816 and U.S. Pat. No. 4,904,650) and 6-alkenylen-androsta-1,4-dien-17-ol-3-one derivatives (U.S. Pat. No. 4,873,233).

Non fluorinated 4-aminoandrostadienone derivatives are disclosed in U.S. Pat. No. 4,757,061.

The present invention provides a compound of formula (I)

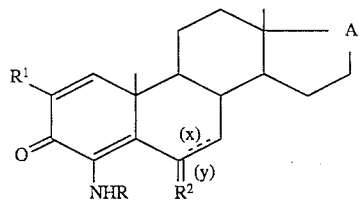

wherein
(x) and (y) are single or double bonds;
A is >C=O or >CH$\sim$OR$^3$;
each of R and R$^3$ are independently hydrogen or acyl;
R$^1$ is hydrogen or fluorine;
and wherein
when (y) is a single bond, R$^2$ is hydrogen, fluorine, methyl or trifluoromethyl; and
when (y) is a double bond, R$^2$ is methylene;
provided that when one of (x) or (y) is a double bond the other is a single bond and provided that at least one of R$^1$ and R$^2$ is fluorine or in the case of R$^2$, trifluoromethyl; and the pharmaceutically acceptable salts thereof.

The invention includes within its scope all the possible isomers, stereoisomers and their mixtures, and the metabolites and the metabolic precursors or bioprecursors of the compound of formula (I). In the formulae of the specification the heavy solid lines ( ▬▬ ) indicate that a substituent is in the β-configuration, i.e. above the plane of the ring, whereas a dotted line ( . . . ) indicates that a substituent is in the α-configuration, i.e. beneath the plane of the ring, and a wavy line ( $\sim$ ) indicates that a substituent may be either in the α-configuration or in the β-configuration or both, i.e. a mixture thereof.

In particular when in the compounds of formula (I) A is >CH$\sim$OR$^3$ the OR$^3$ substituent may be either in the α- in the β-configuration or both; i.e. a mixture thereof. Analogously, when (x) and (y) are single bonds, the R$^2$ substituent may be either in the α- or β-configuration or both.

The present invention includes all the possible isomers, e.g. the single 6α, 17α; 6α, 17β; 6β, 17α and 6β, 17β epimers, as well as all possible mixtures thereof, e.g. 6(α,β), 17α; 6(α,β), 17β; 6α, 17(α,β); 6β, 17(α,β) and 6(α,β), 17(α,β)-isomers of the compounds of formula (I). Hence a compound of the invention herein specifically mentioned, without any indication of its stereo-chemistry, is intended to represent all its possible isomers and mixtures thereof.

An acyl group may be a residue of any physiologically tolerable acid. Preferred examples of said acids are the C$_1$–C$_4$ alkanoic ones, in particular acetic, propionic and butyric acids. The acyl group is therefore preferably a C$_1$–C$_4$ alkanoyl group, more preferably a C$_2$–C$_4$ alkanoyl group, such as acetyl, propionyl or butyryl.

Pharmaceutically acceptable salts of the compounds of the invention include acid addition salts with inorganic acid, e.g. with hydrochloric, hydrobromic, sulphuric, perchloric and phosphoric acid or with organic acids, e.g. acetic, propionic, glycolic, lactic, oxalic, malonic, malic, maleic, tartaric, citric, benzoic, cinnamic, mandelic and salicylic acid.

As stated above, the present invention also includes within its scope pharmaceutically acceptable bioprecursors (otherwise known as pro-drugs) of the compounds of formula (I), i.e. compounds which have a different formula to formula (I) above but which nevertheless upon administration to a human being are converted directly or indirectly in vivo into a compound of formula (I).

Preferred compounds of the invention are the compounds of formula (I) wherein A is a >C=O group, and R is hydrogen, and the pharmaceutically acceptable salts thereof.

Examples of specific compounds of the invention are the following compounds:
4-amino-2-fluoro-androsta-1,4-diene-3,17-dione;
4-amino-6α-fluoro-androsta-1,4-diene-3,17-dione;
4-amino-6β-fluoro-androsta-1,4-diene-3,17-dione;
4-amino-2-fluoro-androsta-1,4,6-triene-3,17-dione;
4-amino-6-fluoro-androsta-1,4,6-triene-3,17-dione;
4-amino-2-fluoro-6-methyl-androsta-1,4,6-triene-3,17-dione;
4-amino-2-fluoro-6-methylen-androsta-1,4-diene-3,17-dione;
4-amino-6α-trifluoromethyl-androsta-1,4-diene-3,17-dione;
4-amino-6β-trifluoromethyl-androsta-1,4-diene-3,17-dione;
4-amino-6-trifluoromethyl-androsta-1,4,6-triene-3,17-dione;
4-amino-2-fluoro-6α-methyl-androsta-1,4-diene-3,17-dione;
4-amino-2-fluoro-6β-methyl-androsta-1,4-diene-3,17-dione;

4-amino-2,6-difluoro-androsta-1,4,6-triene-3,17-dione;
4-amino-2,6α-difluoro-androsta-1,4-diene-3,17-dione;
4-amino-2,6β-difluoro-androsta-1,4-diene-3,17-dione;
as well as, where appropriate, the α,β-mixtures of the above reported 6α, 6β-epimers; and the pharmaceutically acceptable salts thereof.

The compounds of the invention can be obtained by a process comprising:

a) epoxide cleavage with hydrogen fluoride of a compound of formula (II)

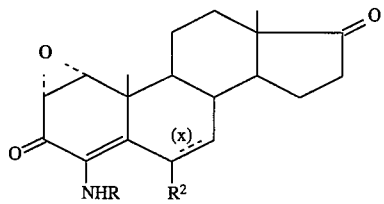

wherein (x) is a single or double bond R is acyl and $R^2$ is hydrogen, methyl or trifluoromethyl so obtaining a compound of formula (I) wherein A is >C=O (x) is a single or double bond, (y) is a single bond, R is acyl, $R^1$ is fluorine and $R^2$ is hydrogen, methyl or trifluoromethyl; or b) epoxide cleavage with hydrogen fluoride of a compound of formula (III)

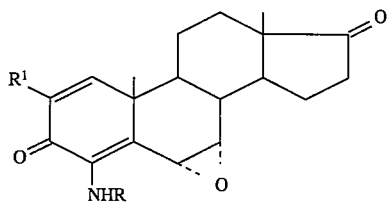

wherein R is acyl and $R^1$ is hydrogen or fluorine, so obtaining a compound of formula (I) wherein A is >C=O (x) is a double bond, (y) is a single bond, R is acyl, $R^1$ is hydrogen or fluorine and $R^2$ is fluorine; or c) fluorination of a compound of formula (IV)

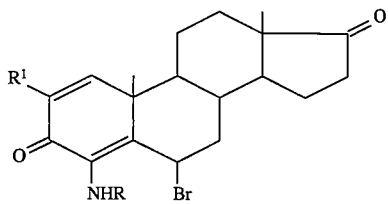

wherein R is acyl and $R^1$ is hydrogen or fluorine, so obtaining a compound of formula (I) in which A is >C=O (x) and (y) are single bonds, R is acyl, $R^1$ is hydrogen or fluorine and $R^2$ is fluorine; or d) selective reduction of the azide compound of formula (V)

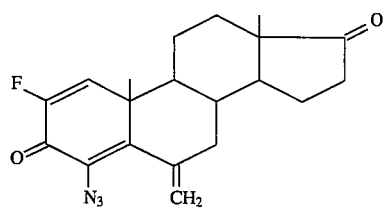

so obtaining a compound of formula (I) wherein A is >C=O (x) is a single bond, (y) is a double bond, R is hydrogen, $R^1$ is fluorine and $R^2$ is methylene; or e) amination of a compound of formula (VI)

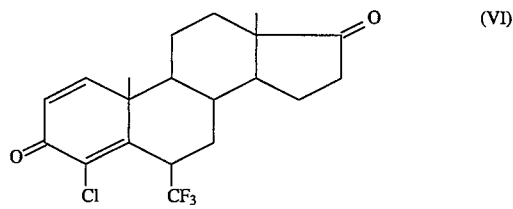

so obtaining a compound of formula (I) in which A is >C=O, (x) and (y) are single bonds, R and $R^1$ are hydrogen and $R^2$ is trifluoromethyl; or f) amination of a compound of formula (VII)

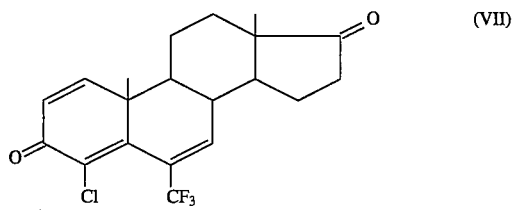

so obtaining a compound of formula (I) wherein A is >C=O (x) is a double bond (y) is a single bond, R and $R^1$ are hydrogen and $R^2$ is trifluoromethyl; and/or g) N-deacylation of a compound of formula (Ia)

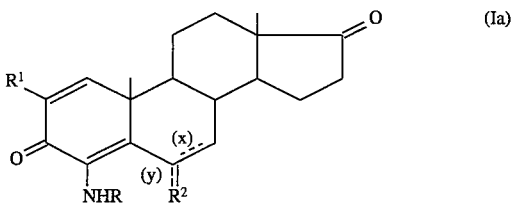

wherein R is acyl and (x), (y), $R^1$ and $R^2$ are as defined above, so obtaining a compound of formula (I) in which A is >C=O, R is hydrogen and x, y, $R^1$ and $R^2$ are as defined above; and/or h) selective reduction of a compound of formula (Ib)

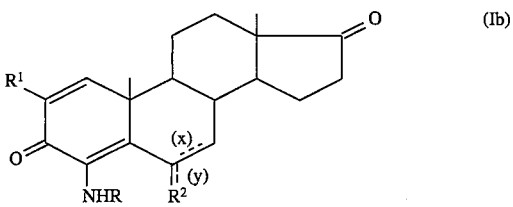

wherein R, $R^1$, $R^2$, (x) and (y) are as defined above thus obtaining compounds of formula (I) wherein A is >CH OH and (x) (y) R, $R^1$ and $R^2$ are as defined above; and/or i) acylation of a compound of formula (Ic)

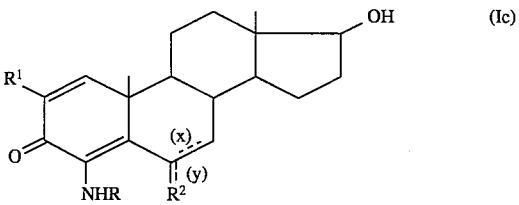

wherein R is acyl and (x), (y), $R^1$ and $R^2$ are as defined above so obtaining a compound of formula (I) wherein R is acyl, (x), (y), $R^1$, $R^2$ are as defined above and A is >CH～OR$^3$ wherein $R^3$ is acyl; and/or j) acylation of a compound of formula (Id)

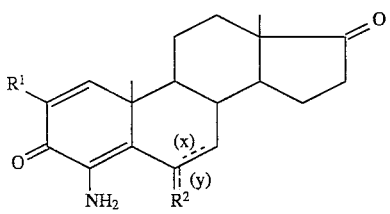

wherein (x), (y), $R^1$ and $R^2$ are as defined above, so obtaining a compound of formula (I) wherein (x), (y), $R^1$ and $R^2$ are as defined above A is >C=O and R is acyl; and/or k) selective O-acylation of a compound of formula (Ie)

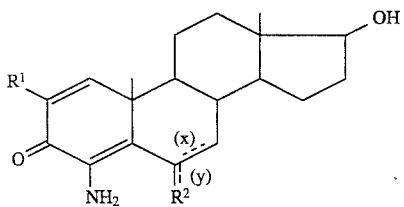

wherein (x), (y), $R^1$ and $R^2$ are as defined above so obtaining a compound of formula (I) wherein (x), (y), $R^1$ and $R^2$ are as defined above and A is >CH—OR$^3$ wherein $R^3$ is acyl;
and/or if desired, converting a compound of formula (I) into another compound of formula (I); and/or, if desired, converting a compound of formula (I) into a salt thereof; and/or, if desired, converting a salt thereof into the corresponding free compound; and/or, if desired, separating a mixture of isomers of a compound of formula (I) into the single isomers.

The epoxide cleavage with hydrogen fluoride of a compound of formula (II) or (III) according, respectively, to the process steps a) and b) in order to obtain an unstable fluorohydrin intermediate, which dehydrates under acidic conditions to give the desired 2-fluoro-$\Delta^1$- or 6-fluoro-$\Delta^6$- compound respectively, may be performed according to known procedures. Preferably it is carried out by reaction with anhydrous hydrofluoric acid in an inert organic solvent such as tetrahydrofuran, chloroform or mixtures thereof at temperatures ranging from about −78° C. to room temperature.

The fluorination according to process step c), that is the bromine-fluorine exchange reaction, may be performed according to known methods, e.g. as described by J. Mann et al. in J. Chem. Soc. Perkin Trans. I, 2681 (1983). Thus the bromo compound is reacted with pyridine poly-hydrogen fluoride in the presence of mercury (II) oxide at temperatures ranging from about 0° C. to about 80° C.

The reduction of the azido group according to process step d) may be carried out following known methods, for instance, with a variety of reducing agents, e.g. propane-1, 3-dithiol in triethylamine as described in Tetr. Lett. 39, 3633 (1978); dithiolthreitol in aqueous solution; mercaptoacetic acid and triethylamine or e.g. triphenylphosphine in aqueous tetrahydrofuran as described e.g. in Bull. Soc. Chem. Fr. 1985, 815.

The amination reaction according to process step e) and f) may be performed according to known method, e.g. as described in U.S. Pat. No. 4,865,766.

Preferably a compound of formula (VI) or (VII) is reacted with a concentrated aqueous solution of ammonia in a solvent consisting of mixtures of water and water miscible organic solvents, such as dioxane or tetrahydrofuran, preferably mixtures of water and dioxane. A particularly preferred ratio of such a mixture is 2 parts of 30% aqueous ammonia and 1 part of dioxane. The reaction temperature may range from about 20° C. to about 120° C.

The N-deacylation according to process step g) may be performed by known methods.

Preferably it is carried out by treatment with hydrochloric acid in alcoholic solution at temperatures ranging from about 0° C. to reflux temperature. More preferably it is carried out with conc. hydrochloric acid in boiling ethanol solution. The reduction of the 17-carbonyl group as in process step h) may be carried out by well known methods, e.g. as described by Djerassi in Steroid Reactions (1963) or by Fried in "Organic Reactions in Steroid Chemistry" (1972). Preferably the reduction is carried out with complexed metal hydrides, in particular with sodium borohydride in an inert organic solvent, preferably in methanol solution at temperatures ranging from about 0° C. to about 50° C.

The acylation of the 17-hydroxy group according to process step i) and the acylation of the 4-amino group according to process step j) can be performed, e.g., by reaction with a reactive derivative of a suitable carboxylic acid, such as an anhydride or halide, in the presence of a basic agent, at temperatures ranging from about 0° C. to about 50° C.

Preferably the acylation is carried out by reaction with the respective anhydride in the presence of an organic base such as pyridine.

The selective O-acylation, according to process step k), may be performed by reacting a compound of formula (Ie) in the salt form, e.g. the HCl or $H_2SO_4$ or p-toluene sulfonic acid (PTSA) salt, with the appropriate carboxylic acid of formula $R^3OH$ wherein $R^3$ is acyl in an inert solvent, such as $CHCl_3$, and in the presence of the corresponding acid catalyst, i.e. HCl or $H_2SO_4$ or PTSA, at a temperature ranging from 20° to 100° C. Preferably the reaction is carried out by reacting the PTSA salt of the compound of formula (Ie) with the appropriate carboxylic acid in refluxing $CHCl_3$ solution with azeotropic water removal.

The optional salification of a compound of formula (I) as well as the conversion of a salt into the corresponding free compound and the separation of a mixture of isomers into the single isomers as well as the conversion of a compound of formula (I) into another compound of formula (I) may be carried out according to known methods.

For example the conversion of 17β-hydroxy compound of formula (I) into the corresponding 17α-hydroxy compound may be carried out by basic catalysis, e.g. with 0.1N sodium hydroxide in an aliphatic alcohol such as ethanol. Another example is the conversion of the 6β-fluoro compound of formula (I) into the corresponding 6α-fluoro compound. This isomerization reaction may be carried out by acid catalysis, e.g. with hydrochloric acid in acetic acid. A further example is the isomerization of the 6β-methyl or 6β-trifluoromethyl compounds of formula (I) into the corresponding 6α-compounds. This isomerization reaction may be performed by acid catalysis, e.g. with hydrochloric acid in ethanol solution, or by basic catalysis, e.g. with sodium hydroxide in alcohol solution. A further example is the conversion of the 17-keto compound of formula (I) into the corresponding 17-hydroxy compound of formula (I). This reduction may be carried out by the method reported above. Finally the N-deacylation as described in process step g) and the O-acylation as mentioned in process step i) are other examples for the conversion of a compound of formula (I) into another compound of formula (I).

A compound of formula (II) can be obtained by alkaline epoxidation of a compound of formula (VIII)

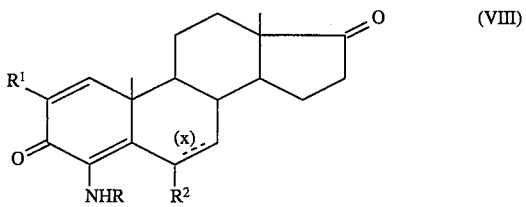

wherein R is acyl, $R^1$ is hydrogen, $R^2$ is hydrogen trifluoromethyl or methyl and (x) is single or double bond. The alkaline epoxidation may be carried out by treatment with a suitable oxidizing agent, e.g. 36% $H_2O_2$ in hydroalcoholic alkali hydroxide solution, preferably KOH or NaOH in methanol, at a temperature ranging from about 0° C. to about 30° C. for reaction times lasting from 2h to several days.

The compounds of formula (VIII) wherein $R^2$ is hydrogen or methyl are known or may be obtained by known methods from known compounds, e.g. as described in U.S. Pat. No. 4,757,061. The compounds of formula (VIII) wherein $R^2$ is trifluoromethyl may be obtained as described in process step (e) and (f).

A compound of formula (III) can be obtained by acidic epoxidation of a compound of formula (IX)

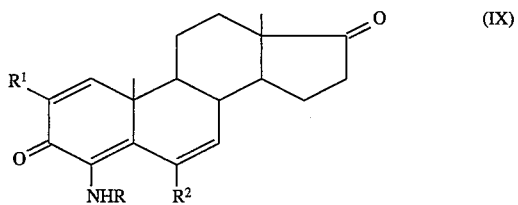

wherein R is acyl, $R^1$ is hydrogen or fluorine and $R^2$ is hydrogen. The acidic epoxidation may be performed by known methods, e.g. by treatment with a suitable organic peracid such as perphthalic, perbenzoic or m-chloroperbenzoic acid, preferably m-chloroperbenzoic acid, in an inert organic solvent such as dichloromethane, chloroform or benzene, preferably dichloromethane, at temperature ranging from about 0° C. to about 50° C.

The compounds of formula (IX) wherein R is acyl and $R^1$ and $R^2$ are hydrogen, are known and may be obtained according to U.S. Pat. No. 4,757,061. The compounds of formula (IX) wherein R is acyl, $R^1$ is fluorine and $R^2$ is hydrogen are obtained as exemplified in process step a).

A compound of formula (IV) can be obtained by allylic bromuration of a compound of formula (X)

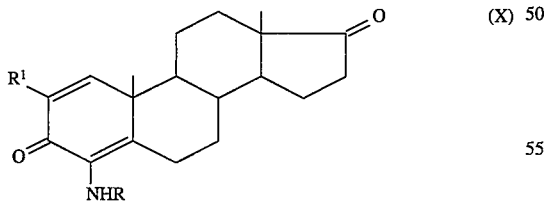

wherein R is acyl and $R^1$ is hydrogen or fluorine. The allylic bromination may be carried out with a brominating agent, such as N-bromosuccinimide, in an inert solvent, e.g. carbon tetrachloride, under reaction conditions well known to the skilled in the art.

The compounds of formula (X) wherein R is acyl and $R^1$ is hydrogen are known and are described in U.S. Pat. No. 4,757,061. The compounds of formula (X) wherein R is acyl and $R^1$ is fluorine may be obtained as described in process step a).

The compounds of formula (V) can be obtained by reacting a compound of formula (XI)

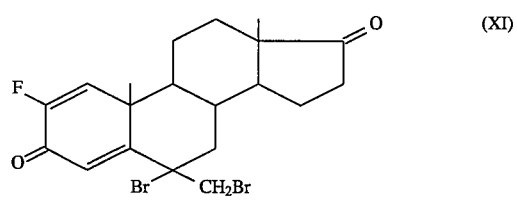

with an alkali or ammonium or trialkylsilyl azide, preferably with sodium azide. The reaction is preferably carried out in an organic solvent such as dimethyl-formamide, dimethylacetamide or dimethylsulfoxide; some water or aqueous methanol or ethanol may be added to increase the solubility of the azide salt.

An inorganic base is also added such as sodium, potassium or lithium carbonate. The reaction is performed under mild conditions, that is at low temperatures ranging from about 0° C. to about 60° C. and for short reaction times, e.g. from some minutes to about 1 h. Under more drastic conditions the corresponding amino compound is obtained.

A compound of formula (XI) can be obtained by bromination of a compound of formula (XII)

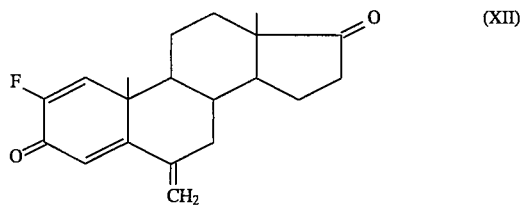

It may be carried out by known methods and under mild conditions e.g. by treatment with bromine in an organic solvent or mixtures thereof, for instance diethyl ether or acetic acid, at temperatures ranging from about –50° C. to 0° C. Preferably only 1 moleq. of bromine is applied.

A compound of formula (XII) can be obtained by epoxide cleavage with hydrogen fluoride of a compound of formula (XIII)

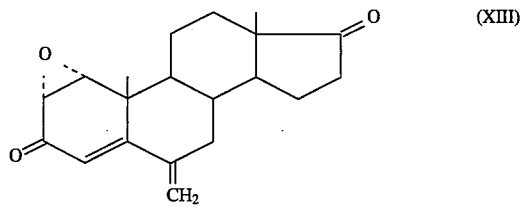

The cleavage may be performed by known procedures. Preferably it is carried out by reaction with anhydrous hydrofluoric acid in an inert organic solvent such as THF, $CHCl_3$ or mixtures thereof at temperatures ranging from about –78° C. to room temperatures.

A compound of formula (XIII) can be obtained by epoxidation of a compound of formula (XIV)

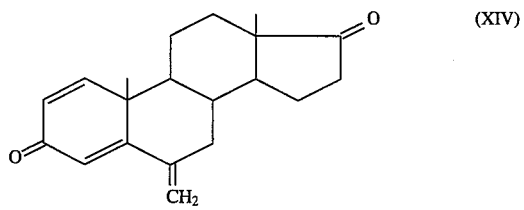

The epoxidation may be carried out by treatment with a suitable oxidizing agent, e.g. 36% H$_2$O$_2$ in hydroalcoholic alkali hydroxide solution, preferably KOH or NaOH in methanol, at a temperatures ranging from about 0° C. to 30° C.

The compound of formula (XIV) is known and may be obtained e.g. according to U.S. Pat. No. 4,808,816.

A compound of formula (VI) can be obtained by chlorination of a compound of formula (XV)

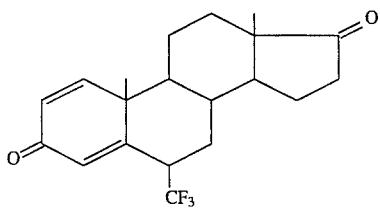

for example using sulfuryl chloride and operating e.g. in pyridine at temperatures ranging from about 0° C. to 60° C.

The compound of formula (XV) can be obtained from a compound of formula (XVI)

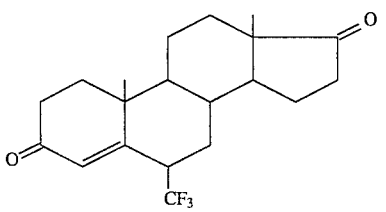

by dehydrogenation with a suitable dehydrogenating agent, e.g. dichlorodicyanobenzoquinone (DDQ), selenium dioxide or chloranil. Preferably such reaction is performed by treatment with DDQ, in an inert solvent, such as dioxane, benzene or toluene at a temperature ranging from about 40° to 110° C. The compound of formula (XVI) is known and may be obtained according to U.K. Pat. 905,694.

The compound of formula (VII) can be prepared, from a compound of formula (XV) as obtained above by allylic bromination with a brominating agent, e.g. N-bromosuccinimide in an inert solvent, e.g. carbon tetrachloride under well known reaction conditions thus giving a 6-bromo derivative.

This is dehydrobrominated in a known way, for example using an organic base, preferably pyridine or collidine, and operating at temperatures ranging from about 20° C. to 130° C. or using an inorganic base, preferably lithium carbonate and lithium chloride in DMF, and operating at temperatures ranging from about 60° C. to 120° C.

When in the new compounds of the present invention and in the intermediate products thereof groups are present, which need to be protected before submitting them to the hereabove illustrated reactions, they may be protected before the reactions take place and then deprotected at the end of the reactions, according to well known methods in organic chemistry.

The compounds of the present invention are inhibitors of the biotransformation of androgens into estrogens, i.e. they are steroidal aromatase inhibitors.

The present invention provides a compound of formula (I), or a pharmaceutically acceptable salt thereof, for use in a method of treatment of the human or animal body by therapy, in particular for use as an aromatase inhibitor.

The present invention also provides the use of a compound of formula (I), or a pharmaceutically acceptable salt thereof, in the preparation of a medicament for use as an aromatase inhibitor.

The aromatase inhibitory activity of these compounds was demonstrated by employing the in vitro test described by Thompson and Siiteri (E.A. Thompson and P. K. Siiteri, J. Biol. Chem. 249, 5364 (1974)) which utilizes the human placental microsomal fraction as enzyme source.

In this test the aromatization rate of androstenedione into estrone was evaluated by incubating (1β-$^3$H) androstenedione (50 nM) in the presence of NADPH with the enzyme preparation and by measuring the amount of $^3$H$_2$O formed during 20 min incubation at 37° C.

The compounds, incubated at various concentrations, showed a relevant aromatase inhibitory activity. By virtue of their ability to inhibit aromatase and, consequently, to reduce estrogen levels, the compounds of the invention are useful in mammals, including humans, in the treatment and prevention of various estrogen-dependent diseases, e.g. breast, endometrial, ovarian and pancreatic cancers, gynecomastia, benign breast disease, endometriosis, polycystic ovarian disease and precocious puberty. Another application of the compounds of the invention is in the therapeutic and/or prophylactic treatment of prostatic hyperplasia, a disease of the estrogen-dependent stromal tissue.

The compounds of the invention can find also use for the treatment of male infertility associated with oligo-spermia and for female fertility control, by virtue of their ability to inhibit ovulation and egg nidation.

In view of their low toxicity the compounds of the invention can be used safely in medicine. For example, the approximate acute toxicity (LD$_{50}$) of the compounds of the invention in the mouse, determined by single administration of increasing doses and measured on the seventh day after the treatment was found to be negligible.

The compounds of the invention can be administered in a variety of dosage forms, e.g. orally, in the form of tablets, capsules, sugar or film coated tablets, liquid solutions or suspensions; rectally, in the form of suppositories, parenterally, e.g. intramuscularly, or by intravenous injection or infusion.

The dosage depends on the age, weight, conditions of the patient and administration route; for example, the dosage adopted for oral administration to adult humans may range from about 10 to about 150–200 mg pro dose, from 1 to 5 times daily.

The invention includes pharmaceutical compositions comprising a compound of the invention in association with a pharmaceutically acceptable excipient (which can be a carrier or diluent).

The pharmaceutical compositions containing the compounds of the invention are usually prepared following conventional methods and are administered in a pharmaceutically suitable form.

For example the solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. a starch, alginic acid, alginates or sodium starch glycolate; effervescing mixtures; dyestuffs, sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes. The liquid dispersion for oral administration may be e.g. syrups, emulsions and suspensions. The syrups may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

The solutions for intravenous injections or infusions may contain as carrier, for example, sterile water or preferably they may be in the form of sterile, aqueous, isotonic saline solutions.

The suppositories may contain together with the active compound a pharmaceutically acceptable carrier, e.g. cocoabutter, polyethylene glycol, a polyoxyethylene sorbitan fatty acid ester surfactant or lecithin.

The following examples illustrate but do not limit the invention:

EXAMPLE 1

4-amino-2-fluoro-androsta-1,4,6-triene-3,17-dione
(I, A=>C=O, R=R$^2$=H, R$^1$=F, x=double bond)

To a solution of anhydrous hydrogen fluoride (6 g) in tetrahydrofuran (11.8 g) and chloroform (6 ml) contained in a screw-capped polyethylene bottle chilled to about −60° C. was added a solution of 4-acetamino-1,2α-epoxy-androsta-4,6-diene-3,17-dione (3.554 g, 10 mmol) in chloroform (30 ml) likewise chilled to about −60° C. The hydrogen fluoride-tetrahydrofuran reagent was immersed in an acetone-dry ice bath while the steroid was being added. Additional chloroform (6 ml) was used to aid the transfer of the epoxide. Subsequently the reaction mixture was maintained at −30° C. for 4 h and then added gradually to a well agitated mixture of an aqueous solution of potassium carbonate, chloroform and ice. The organic layer was separated, the alkaline aqueous layer back-extracted twice with chloroform and the combined organic layers were evaporated to dryness. The residue was submitted to flash chromatography with ethyl acetate-ethanol to give pure 4-acetylamino-2-fluoro-androsta-1,4,6-triene-3,17-dione in 70% yield (2.502 g).

The latter compound (2.502 g, 7 mmol) was dissolved in a mixture of ethanol (140 ml) and 36% hydrochloric acid (14 ml) and heated for 4 h at reflux. The solution was concentrated under vacuum after dilution with water and then extracted 2× with ethyl acetate. The separated aqueous phase was basified under cooling with sodium carbonate to precipitate almost pure title compound in about 65% yield (1.433 g).

$C_{19}H_{22}FNO_2$ calculated: C 72.35 H 7.03 F 6.02 N 4.44 found: C 72.10 H 6.95 F 6.05 N 4.30 MS m/z 315 IR cm$^{-1}$: 3450, 3350 (NH$_2$), 1745 (CO), 1640 (CO), 1615, 1560 (C=C).

According to the above described procedure and starting from the appropriate compound of formula (II) one can prepare the following compounds:
4-amino-2-fluoro-androsta-1,4-diene-3,17-dione;
4-amino-2-fluoro-6α-methyl-androsta-1,4-diene-3,17-dione;
4-amino-2-fluoro-6β-methyl-androsta-1,4-diene-3,17-dione; and
4-amino-2-fluoro-6-methyl-androsta-1,4,6-triene-3,17-dione.

EXAMPLE 2

4-amino-6-fluoro-androsta-1,4,6-triene-3,17-dione
(I, A=>C=O R=R$^1$=H R$^2$=F x=double bond)

To a solution of anhydrous HF (6 g) in THF (11.8 g) and CHCl$_3$ (6 ml) contained in a screw-capped polyethylene bottle chilled to about −60° C. was added a solution of 4-acetylamino-6,7α-epoxy-androsta-1,4-diene-3,17-dione (3.554 g, 10 mmol) in CHCl$_3$ (30 ml) likewise chilled to about −60° C. The HF-THF reagent was immersed in an acetone-dry ice bath while the steroid was being added. Additional CHCl$_3$ (6 ml) was used to aid the transfer of the epoxide. Subsequently the reaction mixture was maintained at −30° C. for 4 h and then added gradually to a well agitated mixture of an aqueous solution of K$_2$CO$_3$, CHCl$_3$ and ice. The organic layer was separated and the alkaline aqueous layer back-extracted twice with CHCl$_3$. The combined organic layers are evaporated to dryness to give crude 4-acetylamino-6β-fluoro-7α-hydroxy-androsta-1,4-diene-3,17-dione. The residue was dissolved in a mixture of ethanol (100 ml) and 36% HCl (10 ml) and heated for 4 h at reflux. The solution was diluted with water, concentrated under vacuum and then extracted 2× with EtOAc. The acid layer was alkalized under cooling with Na$_2$CO$_3$ to precipitate the crude product, which was submitted to flash chromatography with EtOAc-EtOH to give pure title compound in 50% yield (1.577 g).

$C_{19}H_{22}FNO_2$ calculated: C 72.35 H 7.03 F 6.02 N 4.44 found: C 72.10 H 6.80 F 5.85 N 4.35 MS m/z 315 IR cm$^{-1}$: 3450, 3300 (NH$_2$), 1740 (CO), 1635 (CO), 1610, 1570 (C=C).

According to the above described procedure and starting from the appropriate compound of formula (III) one can prepare the following compound: 4-amino-2,6-difluoro-androsta-1,4,6-triene-3,17-dione.

EXAMPLE 3

4-amino-6α-fluoro-androsta-1,4-diene-3,17-dione
and
4-amino-6β-fluoro-androsta-1,4-diene-3,17-dione (I A=>C=O, R=R$^1$=H, R$^2$=F, x=single bond)

A crude mixture of 6α- and 6β-bromo-4-acetylamino-androsta-1,4-diene-3,17-dione (3.78 g, 9 mmol) was added to a vigorously stirred suspension of yellow HgO (3.906 g, 18 mmol) in pyridinium poly-hydrogen fluoride (25 ml) at room temperature. After 3 h the mixture was poured onto crushed ice and extracted with CH$_2$Cl$_2$. The combined extracts were washed, dried and evaporated. The residue was submitted to flash chromatography with EtOAc to give a mixture of 6α- and 6β-fluoro-4-acetylamino-androsta-1,4-diene-3,17-dione in about 60% yield (1.941 g).

The latter product mixture (1.941 g, 5.4 mmol) was dissolved in EtOH (100 ml) and 36% HCl (10 ml) and the solution heated for 4 h at reflux. After dilution with water and concentration under vacuum the solution was extracted twice with EtOAc. The aqueous phase was basified under cooling with Na$_2$CO$_3$ to precipitate a mixture of 6α- and 6β-isomers, which were separated by flash chromatography on silica gel with EtOAc/EtOH 1%. The 4-amino-6-fluoro-androsta-1,4-diene-3,17-dione was obtained in about 20% yield.

$C_{19}H_{24}FNO_2$ calculated: C 71.90 H 7.62 F 5.99 N 4.41 found: C 71.81 H 7.51 F 5.85 N 4.35 MS m/z 317 IR cm$^{-1}$: 3400, 3300 (NH$_2$), 1745 (CO), 1635 (CO), 1610, 1570 (C=C).

The 4-amino-6β-fluoro-androsta-1,4-diene-3,17-dione was obtained in about 30% yield.

$C_{19}H_{24}FNO_2$ calculated: C 71.90 H 7.62 F 5.99 N 4.41 found: C 71.85 H 7.55 F 5.80 N 4.30 MS m/z 317 IR cm$^{-1}$: 3450, 3350 (NH$_2$), 1740 (CO), 1640 (CO), 1610, 1570 (C=C).

According to the above described procedure and starting from the appropriate compound of formula (III) one can prepare the following compounds:
4-amino-2,6α-difluoro-androsta-1,4-diene-3,17-dione; and
4-amino-2,6β-difluoro-androsta-1,4-diene-3,17-dione.

EXAMPLE 4

4-amino-2-fluoro-6-methylen-androsta-1,4-diene-3,17-dione (I, A=>C=O, R=H, R$^1$=F, R$^2$ is=CH$_2$)

To a solution of 4-azido-2-fluoro-6-methylen-androsta-1,4-diene (3.554 g, 10 mmol) in THF (20 ml) was added portionwise triphenylphosphine (2.623 g).

The reaction was exothermic (temperature raise to about 35° C.) and nitrogen evolution could be observed. After about 2.5 h the reaction was terminated (TLC monitoring). Then dioxane (100 ml) and H$_2$O (10 ml) was added and the mixture heated to reflux for 10 h. Finally the mixture was poured onto water and the product extracted with EtOAc. The organic phase was extracted 4× with 2N HCl, the water phase was separated and the almost pure title compound precipitated by neutralization with NaOH. Yield 40%.

$C_{20}H_{24}FNO_2$ calculated: C 72.92 H 7.34 F 5.77 N 4.25 found: C 72.85 H 7.35 F 5.68 N 4.15 MS m/z 329 IR cm$^{-1}$: 3400 (NH$_2$), 3070 (C=CH$_2$), 1725 (17-keto), 1650 (3-keto), 1610 (C=C).

EXAMPLE 5

4-amino-6α-trifluoromethyl-androsta-1,4-diene-3,17-dione (I A=>C=O, R=R$^1$=H, R$^2$=CF$_3$, x=y=single bond)

A mixture of 4-chloro-6α-trifluoromethylandrosta-1,4-diene-3,17-dione (1.161 g, 3 mmol), dioxane (30 ml) and 30% NH$_9$OH (60 ml) was stirred at 75° C. in a pressure vessel during 18 h. After cooling to room temperature the solvent and excess of ammonia was evaporated in vacuo and the residue was acidified to pH 1 by adding HCl conc. The aqueous solution was washed twice with EtOAc and brought to pH 11 by carefully adding conc. NaOH. The resulting precipitate was filtered off, washed with water and dried under vacuum at 40° C. The almost pure title compound was obtained in about 30% yield.

$C_{20}H_{24}F_3NO_2$ calculated: C 65.38 H 6.58 F 15.51 N 3.81 found: C 65.25 H 6.45 F 15.45 N 3.75 MS m/z 367 IR cm$^{-1}$: 3450, 3300 (NH$_2$), 1745 (CO), 1645 (CO), 1610, 1570 (C=C).

By proceeding analogously and starting from the 6β-trifluoromethyl isomer of formula (VI) the following compound can be prepared:
4-amino-6β-trifluoromethyl-androsta-1,4-diene-3,17-dione.

EXAMPLE 6

4-amino-6-trifluoromethyl-androsta-1,4,6-triene-3,17-dione (I, A is >C=O, R=R$^1$=H, R$^2$=CF$_3$, x=double bond)

A mixture of 4-chloro-6-trifluoromethylandrosta-1,4,6-triene-3,17-dione (1.924 g, 5 mmol), dioxane (50 ml) and 30% NH$_9$OH (100 ml) was stirred at 90° C. in pressure vessel during 24 h. After cooling to room temperature the reaction mixture was worked up as described in the Example 5. There are obtained 0.457 g (25% yield) of the title compound as a yellow solid.

$C_{20}H_{22}F_3NO_2$ calculated: C 65.74 H 6.07 F 15,60 N 3.83 found: C 65.65H 6.03 F 15.55 N 3.75 MS m/z 365 IR cm$^{-1}$: 3350 (NH$_2$), 1740 (CO), 1635 (CO), 1605, 1570 (C=C).

EXAMPLE 7

4-amino-2-fluoro-androsta-1,4,6-triene-3,17-dione (I, R=R$^2$=H, R$^1$=F, A is >C=O, x=double bond).

4-acetylamino-2-fluoro-androsta-1,4,6-triene-3,17-dione (2.502 g, 7 mmol) was dissolved in a mixture of EtOH (140 ml) and 36% HCl (14 ml) and heated for 4 h at reflux. The solution was concentrated under vacuum after dilution with water and then extracted 2× with EtOAc.

The separated aqueous phase was made alkaline by Na$_2$CO$_3$ addition under cooling to precipitate almost pure title compound in about 65% yield (1.433 g).

By proceeding analogously and starting from the appropriate acylamino compound of formula (I) the following compound can be prepared:
4-amino-2-fluoro-androsta-1,4-diene-3,17-dione;
4-amino-2-fluoro-6α-methyl-androsta-1,4-diene-3,17-dione;
4-amino-2-fluoro-6β-methyl-androsta-1,4-diene-3,17-dione;
4-amino-2-fluoro-6-methyl-androsta-1,4,6-triene-3,17-dione;
4-amino-6-fluoro-androsta-1,4,6-triene-3,17-dione;
4-amino-2,6-difluoro-androsta-1,4,6-triene-3,17-dione;
4-amino-6α-fluoro-androsta-1,4-diene-3,17-dione;
4-amino-6β-fluoro-androsta-1,4-diene-3,17-dione;
4-amino-2,6α-difluoro-androsta-1,4-diene-3,17-dione; and
4-amino-2,6β-difluoro-androsta-1,4-diene-3,17-dione.

EXAMPLE 8

4-amino-2-fluoro-androsta-1,4,6-triene-17β-ol-3-one (I, A is >CH—OH, R=R$^2$=H, R$^1$=F, x=double bond)

To a stirred solution of 4-amino-2-fluoro-androsta-1,4,6-triene-3,17-dione (3.154 g, 10 mmol) in methanol (200 ml) was added sodium borohydride (0.570 g, 15 mmol) over a period of 20 min at 0°–5° C. and stirring was continued for another 1 hour at 0°–5° C. After addition of few drops of acetic acid, the mixture was concentrated under vacuum, diluted with water and extracted with ethyl acetate. The combined organic phases were washed with saline solution, dried (Na$_2$SO$_4$) and then evaporated in vacuum. The residue was submitted to column chromatography on silica gel. Gradient elution with ethylacetate-ethanol mixtures afforded pure title compound in 80% yield.

$C_{19}H_{24}FNO_2$ calculated: C 71.90 H 7.62 F 5.99 N 4.41 found: C 71.65 H 7.45 F 6.01 N 4.50 MS m/z 317 IR cm$^{-1}$: 3400, 3300 (NH$_2$, OH), 1640 (CO), 1610, 1570 (C=C).

EXAMPLE 9

4-acetylamino-17β-acetoxy-2-fluoro-androsta-1,4,6-triene-3-one (I, A is >CH—OAc, R=Ac, R$^1$=F, R$^2$=H, x=double bond)

To a cooled solution of 4-acetylamino-17β-hydroxy-2-fluoro-androsta-1,4,6-triene-3-one (3.594 g, 10 mmol) in dry pyridine (5 ml) was added acetic anhydride (4.084 g, 40 mmol) and the mixture maintained at 0°–5° C. overnight. The solvent was removed in vacuum, the residue dissolved in CH$_2$Cl$_2$, the organic layer washed with water and then evaporated under reduced pressure. The crude product was crystallized from benzene to yield pure title compound in 80% yield (3.212 g).

$C_{23}H_{28}FNO_4$ calculated: C 68.81 H 7.03 F 4.73 N 3.49 found: C 68.75 H 7.05 F 4.65 N 3.35 MS m/z 401 IR cm$^{-1}$: 3400, 3200 (NH), 1740 (OCOCH$_3$), 1680 (—NHCOCH$_3$), 1630 (3-keto).

EXAMPLE 10

4-amino-2-fluoro-androsta-1,4,6-triene-3,17-dione hydrochloride (I, A is >C=O, R=R$^2$=H, R$^1$=F, x=double bond)

A solution of 4-amino-2-fluoro-androsta-1,4,6-triene-3,17-dione (3.154 g, 10 mmol) in ethanol (100 ml) was treated with 0.1N hydrochloric acid (100 ml, 10 mmol).

The yellow solution was then treated with 0.1 g carbon filtered and the alcohol distilled off at reduced pressure. The resulting aqueous solution was liophilized to give pure title compound in 100% yield (3.518 g).

$C_{19}H_{23}ClFNO_2$ calculated: C 64.86 H 6.59 Cl 10.08 N 3.98 found: C 64.75 H 6.55 Cl 10.01 N 3.90 MS m/z 351.

EXAMPLE 11

4-acetamino-1,2α-epoxy-androsta-4,6-diene-3,17-dione (II, R=COCH$_3$, R$^2$=H, x=double bond)

To an ice cold solution of 4-acetamino-androsta-1,4,6-triene-3,17-dione (3.384 g, 10 mmol) in methanol (50 ml) and CH$_2$Cl$_2$ (25 ml) are added gradually 35% H$_2$O$_2$ (4.5 ml) and 2N NaOH (1 ml). The mixture was allowed to stand at 0°–5° C. for 5 days. Then ice water was added, the mixture concentrated under vacuum to a small volume and the precipitate filtered off. Thus almost pure title compound was obtained (1.99 g). From the mother liquor 1.020 g of starting product was recovered. Therefore the yield is about 80% considering the recovery.

$C_{21}H_{25}NO_4$ calculated: C 70.96 H 7.09 H 3.94 found: C 70.88 H 7.05 N 3.95 MS m/z 355.

According to the above described procedure and starting from the appropriate compound of formula (VIII) the following compounds can be prepared:
4-acetamino-1,2α-epoxy-androst-4-ene-3,17-dione;
4-acetamino-1,2α-epoxy-6-methyl-androsta-1,4-diene-3,17-dione; and
4-acetamino-1,2α-epoxy-6-methyl-androst-4-ene-3,17-dione.

EXAMPLE 12

4-acetamino-6,7-epoxy-androsta-1,4-diene-3,17-dione (III, R=COCH$_3$, R$^1$=H)

To a stirred solution of 4-acetamino-androsta-1,4,6-triene-3,17-dione (3.384 g, 10 mmol) in CH$_2$Cl$_2$ (100 ml) was added borate buffer of pH 8 (50 ml) and then gradually 50% m-chloroperbenzoic acid (6.9 g, 20 mmol) under cooling. The mixture was stirred for 6 h at room temperature until total conversion (TLC monitoring). The mixture was then stirred with 20% sodium metabisulfite solution for 1 h at room temperature. Finally the organic phase was separated, dried and evaporated under vacuum. The residue was submitted to flash chromatography on silica gel with EtOAc thus giving pure title compound in 50% yield (1.772 g).

$C_{21}H_{25}NO_4$ calculated: C 70.96 H 7.09 N 3.94 found: C 70.71 H 6.99 N 3.85 MS m/z 355.

According to the above described procedure and starting from the appropriate compound of formula (IX) the following compound can be prepared:
4-acetamino-6,7α-epoxy-2-fluoro-androsta-1,4-diene-3,17-dione.

EXAMPLE 13

6α-and 6β-bromo-4-acetamino-androsta-1,4-diene-3,17-dione (IV, R$^1$=H).

To a solution of 4-acetamino-androsta-1,4-diene-3,17-dione (3.404 g, 10 mmol) in CCl$_4$ (250 ml) were added N-bromosuccinimide (2.850 g, 16 mmol) and benzoyl peroxide (0.121 g, 0.5 mmol). The solution was heated under reflux for 1 h and then filtered to remove any insoluble material. The filtrate was washed with 5% NaHCO$_3$ solution and with water and the organic phase evaporated to dryness under reduced pressure. The residue was triturated with a small amount of 95% EtOH to give mixture of crude 6α- and 6α-bromoacetamino-androsta-1,4-diene-3,17-dione in 90% yield (3.780 g), which was used in the following fluorination reaction without further purification.

By proceeding analogously the following compounds can be prepared:
6α-bromo-4-acetamino-2-fluoro-androsta-1,4-diene-3,17-dione; and
6β-bromo-4-acetamino-2-fluoro-androsta-1,4-diene-3,17-dione.

EXAMPLE 14

4-azido-2-fluoro-6-methylen-androsta-1,4-diene-3,17-dione (V)

To a solution of 6β-bromo-6α-bromomethyl-2-fluoro-androsta-1,4-diene-3,17-dione (4.742 g, 10 mmol) in DMF (100 ml) were added Li$_2$CO$_3$ (0.74 g, 10 mmol). To the resulting mixture was added dropwise in ¼ h a solution of NaN$_3$ (0.650 g, 10 mmol) in water (10 ml). The mixture was stirred for further 2 h without cooling. The temperature raises to about 35° C. at the beginning and then falls to room temperature. Then water (400 ml) was added to precipitate the product, which was filtered, washed and dried under vacuum. Thus almost pure title compound was obtained in 80% yield (2.84 g).

$C_{20}H_{22}FN_3O_2$ calculated: C 67.59 H 6.24 F 5.35 N 11.82 found: C 67.51 H 6.15 F 5.25 N 11.75 MS m/z 355.

EXAMPLE 15

6β-bromo-6α-bromomethyl-2-fluoro-androsta-1,4-diene-3,17-dione (XI)

To a suspension of 2-fluoro-6-methylen-androsta-1,4-diene-3,17-dione (3.144 g, 10 mmol) in anhydrous ether (100 ml) cooled to about −5° C. was added dropwise 1 molar bromine solution in acetic acid (10 ml) at about −5° C. in 20 min. The reaction mixture was stirred for further ½ h at about 0° C. (TLC monitoring). Then ethanol was added (50 ml), the ether was evaporated under vacuum and the raw product was precipitated by water addition. The latter was submitted to flash chromatography. Elution with hexane/ethylacetate 20% provided a tetrabromo compound while elution with hexane/ethylacetate 30% gave the title compound in about 60% yield (2.845 g).

$C_{20}H_{23}Br_2FO_2$ calculated: C 50.66 H 4.89 Br 33.70 F 4.01 found: C 50.61 H 4.75 Br 33.72 F 4.05 MS m/z 474.

EXAMPLE 16

2-fluoro-6-methylenandrosta-1,4-diene-3,17-dione (XII)

To a solution of anhydrous hydrogen fluoride (7.00 g, 350 mmol) in tetrahydrofuran (15 ml) and chloroform (5 ml) contained in a screw-capped polyethylene bottle chilled to about −60° C. was added a solution of 1,2α-epoxy-6-methylen-androst-4-ene-3,14-dione (3.124 g, 10 mmol) in chloroform (25 ml) likewise chilled to about −60° C.

The hydrogen fluoride-tetrahydrofuran reagent was immersed in an acetone-dry ice bath while the steroid was added. Additional chloroform (5 ml) was used to aid in the transfer of the epoxide. The reaction mixture was removed from the acetone-dry ice bath and subsequently maintained at −30° C. for 4 h and then added at a suitable rate to a well agitated mixture of an aqueous solution of potassium carbonate, chloroform and ice. The weakly alkaline aqueous layer was separated and twice back-extracted with chloroform. The combined organic layers were washed with water, dried and evaporated to dryness. The residue was submitted to flash chromatography with ethyl acetate/ethanol 1–2% to give pure title compound in 75% yield.

$C_{20}H_{23}O_2$ calculated: C 81.32 H 7.85 F 6.04 found: C 81.21 H 7.75 F 6.01 MS m/z 295 IR cm$^{-1}$: 3070 (C=CH$_2$), 1725 (17-keto), 1650 (3-keto), 1610 (C=C).

According to the above described procedure, the following compounds can be prepared:
2-fluoro-6-methylen-androsta-1,4-dien-17β-ol-3-one;
17β-acetoxy-2-fluoro-6-methylen-androsta-1,4-dien-3-one.

EXAMPLE 17

1,2α-epoxy-6-methylen-androsta-1,4-diene-3,17-dione (XIII)

6-methylen-androsta-1,4-diene-3,17-dione (2.964 g, 10 mmol) was dissolved in methanol (200 ml) and the resulting solution cooled to 0° C. Thereupon ice cold 36% hydrogen peroxide (20 ml) and 2% sodium hydroxide (10 ml) were added. The mixture was stirred for about 24 h at 0° C. and then poured into ice water. The product was filtered off, washed with water and then dried to give almost pure title compound in about 50% yield (15.560 g).

$C_{20}H_{24}O_3$ calculated: C 76.89 H 7.74 found: C 76.85 H 7.65 MS m/z 312 IR cm$^{-1}$: 3060 (C=CH$_2$), 1740 (17-keto), 1715 (3-keto), 1250 (epoxide).

EXAMPLE 18

4-chloro-6α-trifluoromethyl-androsta-1,4-diene-3,17-dione (VI)

To a solution of 6α-trifluoromethyl-androsta-1,4-diene-3,17-dione (3.524 g, 10 mmol) in pyridine (35 ml) was added dropwise sulfurylchloride (2.699 g, 20 mmol) at about +5° C. in 20 min. The reaction mixture was stirred further 1 h at +5° C. and then poured onto water. The precipitate was filtered off and the residue purified by trituration in ethylacetate and dichloromethane. Thus almost pure title compound was obtained in about 60% yield (2.32 g).

$C_{20}H_{22}ClF_3O_2$ calculated: C 62.10 H 5.73 Cl 9.16 F 14.73 found: C 62.05 H 5.65 Cl9.05 F 14.65 MS m/z 386.

EXAMPLE 19

6α-trifluoromethyl-androsta-1,4-diene-3,17-dione (XV)

6α-trifluoromethyl-androst-4-ene-3,17-dione (3.544 g, 10 mmol) and dichlorodicyanobenzoquinone (DDQ, 3.4 g, 15 mmol) were refluxed in anhydrous dioxane (150 ml) for about 10 h. To remove the DDQ the suspension was filtered through alumina. After evaporation of the solvent the residue was dissolved in ethylacetate, the organic layer washed with water, dried (Na$_2$SO$_4$) and then evaporated.

The crude product was submitted to column chromatography using hexane/ethylacetate 40% as eluant to give pure title compound in 50% yield (1.763 g).

$C_{20}H_{23}F_3O_2$ calculated: C 68.17 H 6.58 F 16.17 found: C 68.11 H 6.51 F 16.05 MS m/z 352.

EXAMPLE 20

Tablets each weighing 0.150 g and containing 25 mg of the active substance, were manufactured as follows:

| Composition (for 10,000 tablets): | |
| --- | --- |
| 4-amino-2-fluoro-androsta-1,4,6-triene-3,17-dione | 250 g |
| Lactose | 800 g |
| Corn starch | 415 g |
| Talc powder | 30 g |
| Magnesium stearate | 5 g |

4-amino-2-fluoro-androsta-1,4,6-triene-3,17-dione, the lactose and half the corn starch were mixed; the mixture was then forced through a sieve of 0.5 mm mesh size.

Corn starch (10 g) was suspended in warm water (90 ml) and the resulting paste was used to granulate the powder.

The granulate was dried, comminuted on a sieve of 1.4 mm mesh size, then the remaining quantity of starch, talc and magnesium stearate was added, carefully mixed and processed into tablets.

EXAMPLE 21

Capsules, each dosed at 0.200 g and containing 20 mg of the active substance were prepared.

| Composition for 500 capsules: | |
|---|---|
| 4-amino-6-fluoro-androsta-1,4,6-triene-3,17-dione | 10 g |
| Lactose | 80 g |
| Corn starch | 5 g |
| Magnesium stearate | 5 g |

This formulation was encapsulated in two-piece hard gelatin capsules and dosed at 0.200 g for each capsule.

We claim:

1. A compound of the formula (I):

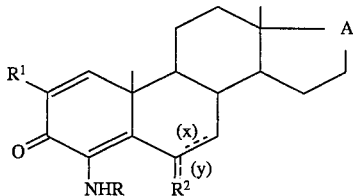

wherein (x) and (y) are each single or double bonds; A is

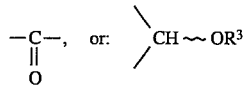

each of R and $R^3$ is independently hydrogen or acyl; $R^1$ is hydrogen or fluorine; and wherein when (y) is a single bond, $R^2$ is hydrogen, fluorine, methyl or trifluoromethyl; and when (y) is a double bond, $R^2$ is methylene;

provided that when one of (x) and (y) is a double bond, the other is a single bond, and that at least one of $R^1$ and $R^2$ is fluorine or $R^2$ is trifluoromethyl; or a pharmaceutically acceptable salt thereof.

2. The compound of the formula (I) of claim 1, wherein A is

and R is hydrogen.

3. The compound of the formula (I) of claim 1, which is selected from the group consisting of:
4-amino-2-fluoro-androsta-1,4-diene-3,17-dione;
4-amino-6α-fluoro-androsta-1,4-diene-3,17-dione;
4-amino-6β-fluoro-androsta-1,4-diene-3,17-dione;
4-amino-2-fluoro-androsta-1,4,6-triene-3,17-dione;
4-amino-6-fluoro-androsta-1,4,6-triene-3,17-dione;
4-amino-2-fluoro-6-methyl-androsta-1,4,6-triene-3,17-dione;
4-amino-2-fluoro-6-methylen-androsta-1,4-diene-3,17-dione;
4-amino-6α-trifluoromethyl-androsta-1,4-diene-3,17-dione;
4-amino-6β-trifluoromethyl-androsta-1,4-diene-3,17-dione;
4-amino-6-trifluoromethyl-androsta-1,4,6-triene-3,17-dione;
4-amino-2-fluoro-6α-methyl-androsta-1,4-diene-3,17-dione;
4-amino-2-fluoro-6β-methyl-androsta-1,4-diene-3,17-dione;
4-amino-2,6-difluoro-androsta-1,4,6-triene-3,17-dione;
4-amino-2,6α-difluoro-androsta-1,4-diene-3,17-dione;
4-amino-2,6β-difluoro-androsta-1,4-diene-3,17-dione; and the α,β-mixtures of the above 6α,6β-epimers; or a pharmaceutically acceptable salt thereof.

4. A pharmaceutical composition for effecting aromatase inhibition in a patient in need thereof, comprising a suitable carrier and a pharmaceutically effective amount of a compound of the formula (I):

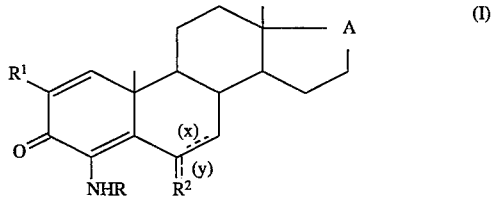

wherein (x) and (y) are each single or double bonds; A is

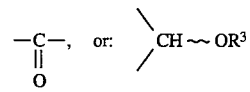

each of R and $R^3$ is independently hydrogen or acyl; $R^1$ is hydrogen or fluorine; and wherein when (y) is a single bond, $R^2$ is hydrogen, fluorine, methyl or trifluoromethyl; and when (y) is a double bond, $R^2$ is methylene;

provided that when one of (x) and (y) is a double bond, the other is a single bond, and that at least one of $R^1$ and $R^2$ is fluorine or $R^2$ is trifluoromethyl; or a pharmaceutically acceptable salt thereof.

5. The pharmaceutical composition of claim 4, wherein in the formula (I), A is

and R is hydrogen.

6. The pharmaceutical composition of claim 4, wherein said compound of the formula (I) is selected from the group consisting of:
4-amino-2-fluoro-androsta-1,4-diene-3,17-dione;
4-amino-6α-fluoro-androsta-1,4-diene-3,17-dione;
4-amino-6β-fluoro-androsta-1,4-diene-3,17-dione;
4-amino-2-fluoro-androsta-1,4,6-triene-3,17-dione;
4-amino-6-fluoro-androsta-1,4,6-triene-3,17-dione;
4-amino-2-fluoro-6-methyl-androsta-1,4,6-triene-3,17-dione;
4-amino-2-fluoro-6-methylen-androsta-1,4-diene-3,17-dione;
4-amino-6α-trifluoromethyl-androsta-1,4-diene-3,17-dione;
4-amino-6β-trifluoromethyl-androsta-1,4-diene-3,17-dione;
4-amino-6-trifluoromethyl-androsta-1,4,6-triene-3,17-dione;
4-amino-2-fluoro-6α-methyl-androsta-1,4-diene-3,17-dione;
4-amino-2-fluoro-6β-methyl-androsta-1,4-diene-3,17-dione;
4-amino-2,6-difluoro-androsta-1,4,6-triene-3,17-dione;
4-amino-2,6α-difluoro-androsta-1,4-diene-3,17-dione;
4-amino-2,6β-difluoro-androsta-1,4-diene-3,17-dione; and the α,β-mixtures of the above 6α,6β-epimers; or a pharmaceutically acceptable salt thereof.

* * * * *